(12) United States Patent
Seligman

(10) Patent No.: US 8,026,637 B2
(45) Date of Patent: Sep. 27, 2011

(54) POWER SUPPLY HAVING AN AUXILIARY POWER CELL

(75) Inventor: Peter Seligman, Essendon (AU)

(73) Assignee: Cochlear Limited, Macquarie University, NSW (AU)

( * ) Notice: Subject to any disclaimer, the term of this patent is extended or adjusted under 35 U.S.C. 154(b) by 352 days.

(21) Appl. No.: 12/179,276

(22) Filed: Jul. 24, 2008

(65) Prior Publication Data

US 2009/0079265 A1  Mar. 26, 2009

Related U.S. Application Data

(63) Continuation-in-part of application No. 11/645,729, filed on Dec. 27, 2006, now Pat. No. 7,638,898, which is a continuation of application No. 10/250,705, filed as application No. PCT/AU02/00074 on Jan. 24, 2002, now Pat. No. 7,157,808.

(30) Foreign Application Priority Data

Jan. 24, 2001 (AU) ..................... PR2693
Jan. 24, 2002 (WO) ............... PCT/AU02/00074

(51) Int. Cl.
*H02J 1/10* (2006.01)
*H02J 1/00* (2006.01)

(52) U.S. Cl. ............... 307/48; 307/64; 307/66; 307/71; 307/86

(58) Field of Classification Search ............ 307/44, 307/50, 71, 80, 85–86, 48, 64, 66
See application file for complete search history.

(56) References Cited

U.S. PATENT DOCUMENTS

| 3,930,192 A | 12/1975 | Dinkler |
| 4,081,738 A | 3/1978 | Roller |
| 4,175,249 A * | 11/1979 | Gruber ................... 323/271 |
| 4,315,162 A | 2/1982 | Ferguson |
| 4,509,193 A | 4/1985 | Carlson |
| 4,532,930 A | 8/1985 | Crosby et al. |
| 4,563,621 A | 1/1986 | Moore |
| 4,614,905 A * | 9/1986 | Petersson et al. ......... 320/122 |
| 4,955,729 A | 9/1990 | Marx et al. |
| 5,003,244 A | 3/1991 | Davis, Jr. |

(Continued)

FOREIGN PATENT DOCUMENTS

WO  WO-9627932  9/1996

(Continued)

OTHER PUBLICATIONS

International Search Report of PCT/AU02/00074, dated Mar. 13, 2002.

(Continued)

*Primary Examiner* — Jared Fureman
*Assistant Examiner* — Adi Amrany
(74) *Attorney, Agent, or Firm* — Kilpatrick, Townsend & Stockton, LLP

(57) ABSTRACT

A power supply having a plurality of selectively electrically connectable power cells configured to supply power to a load. The power supply comprises a plurality of power cells electrically connected in series and an auxiliary power cell electrically connected in parallel with one of said plurality of power cells. A control is configured to selectively electrically connect said auxiliary cell in parallel with whichever one of said plurality of power cells has a lower power delivery capability.

25 Claims, 10 Drawing Sheets

U.S. PATENT DOCUMENTS

| | | | | |
|---|---|---|---|---|
| 5,235,232 | A * | 8/1993 | Conley et al. | 310/303 |
| 5,355,071 | A | 10/1994 | Ishida et al. | |
| 5,387,857 | A * | 2/1995 | Honda et al. | 320/120 |
| 5,488,282 | A * | 1/1996 | Hayden et al. | 320/118 |
| 5,594,320 | A * | 1/1997 | Pacholok et al. | 320/103 |
| 5,666,040 | A * | 9/1997 | Bourbeau | 320/118 |
| 5,687,129 | A | 11/1997 | Kim et al. | |
| 5,696,833 | A | 12/1997 | Matzen et al. | |
| 5,710,504 | A | 1/1998 | Pascual et al. | |
| 5,742,150 | A | 4/1998 | Khuwatsamrit | |
| 5,747,966 | A | 5/1998 | Minamoto et al. | |
| 5,767,660 | A * | 6/1998 | Schmidt | 320/140 |
| 5,814,970 | A * | 9/1998 | Schmidt | 320/118 |
| 5,821,729 | A * | 10/1998 | Schmidt et al. | 320/126 |
| 5,876,425 | A | 3/1999 | Gord et al. | |
| 5,880,575 | A * | 3/1999 | Itou et al. | 320/122 |
| 5,956,241 | A | 9/1999 | LoCascio | |
| 6,031,355 | A | 2/2000 | Rich | |
| 6,064,178 | A * | 5/2000 | Miller | 320/117 |
| 6,157,165 | A * | 12/2000 | Kinoshita et al. | 320/116 |
| 6,222,344 | B1 | 4/2001 | Peterson et al. | |
| 6,268,711 | B1 * | 7/2001 | Bearfield | 320/117 |
| 6,281,662 | B1 * | 8/2001 | Flohr | 320/141 |
| 6,358,281 | B1 | 3/2002 | Berrang et al. | |
| 6,373,226 | B1 * | 4/2002 | Itou et al. | 320/132 |
| 6,518,725 | B2 | 2/2003 | Marten | |
| 6,624,535 | B2 * | 9/2003 | Morrow | 307/71 |
| 6,636,751 | B1 * | 10/2003 | McCartney | 455/572 |
| 6,815,931 | B1 | 11/2004 | Wells et al. | |
| 6,841,971 | B1 * | 1/2005 | Spee et al. | 320/119 |
| 6,879,855 | B2 | 4/2005 | Schulman et al. | |
| 6,983,212 | B2 * | 1/2006 | Burns | 702/63 |
| 7,157,808 | B2 | 1/2007 | Seligman | |
| 7,288,919 | B2 * | 10/2007 | Morita | 320/116 |
| 7,378,818 | B2 | 5/2008 | Fowler et al. | |
| 7,409,068 | B2 | 8/2008 | Ryan et al. | |
| 7,638,898 | B2 | 12/2009 | Seligman | |
| 2002/0109482 | A1 | 8/2002 | Anzawa et al. | |
| 2002/0114982 | A1 * | 8/2002 | Putt et al. | 429/3 |
| 2003/0139888 | A1 | 7/2003 | Burns | |
| 2004/0113586 | A1 | 6/2004 | Chen | |
| 2005/0140335 | A1 | 6/2005 | Lee et al. | |
| 2006/0100674 | A1 | 5/2006 | Molin | |
| 2007/0097719 | A1 | 5/2007 | Parramon et al. | |
| 2009/0085553 | A1 * | 4/2009 | Kumar et al. | 323/351 |
| 2010/0219793 | A1 | 9/2010 | Seligman | |

FOREIGN PATENT DOCUMENTS

WO     WO-02060029     8/2002

OTHER PUBLICATIONS

International Preliminary Examination Report of PCT/AU02/00074, dated Sep. 18, 2002.

International-Type Search Report, issued in connection with Australian Patent Application No. PR 2693, mailed Mar. 7, 2001.

* cited by examiner

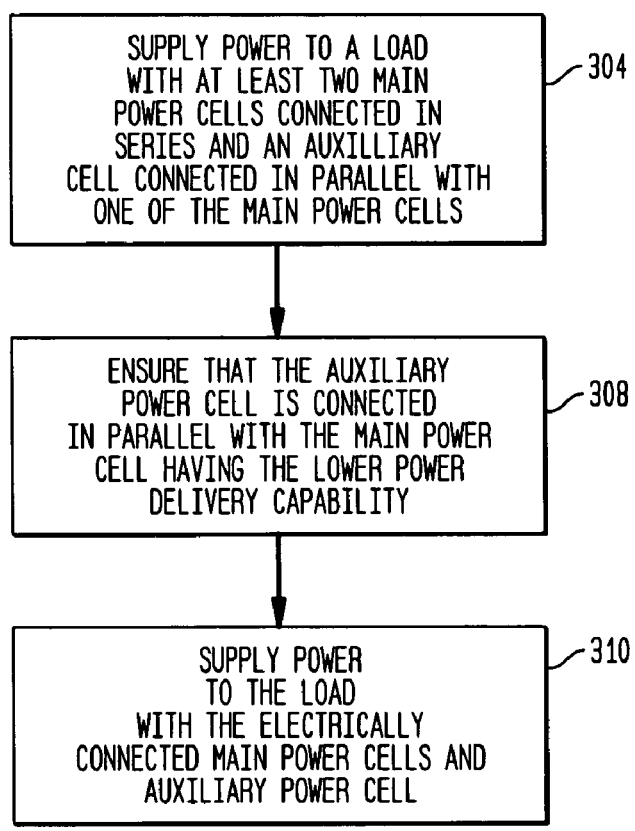

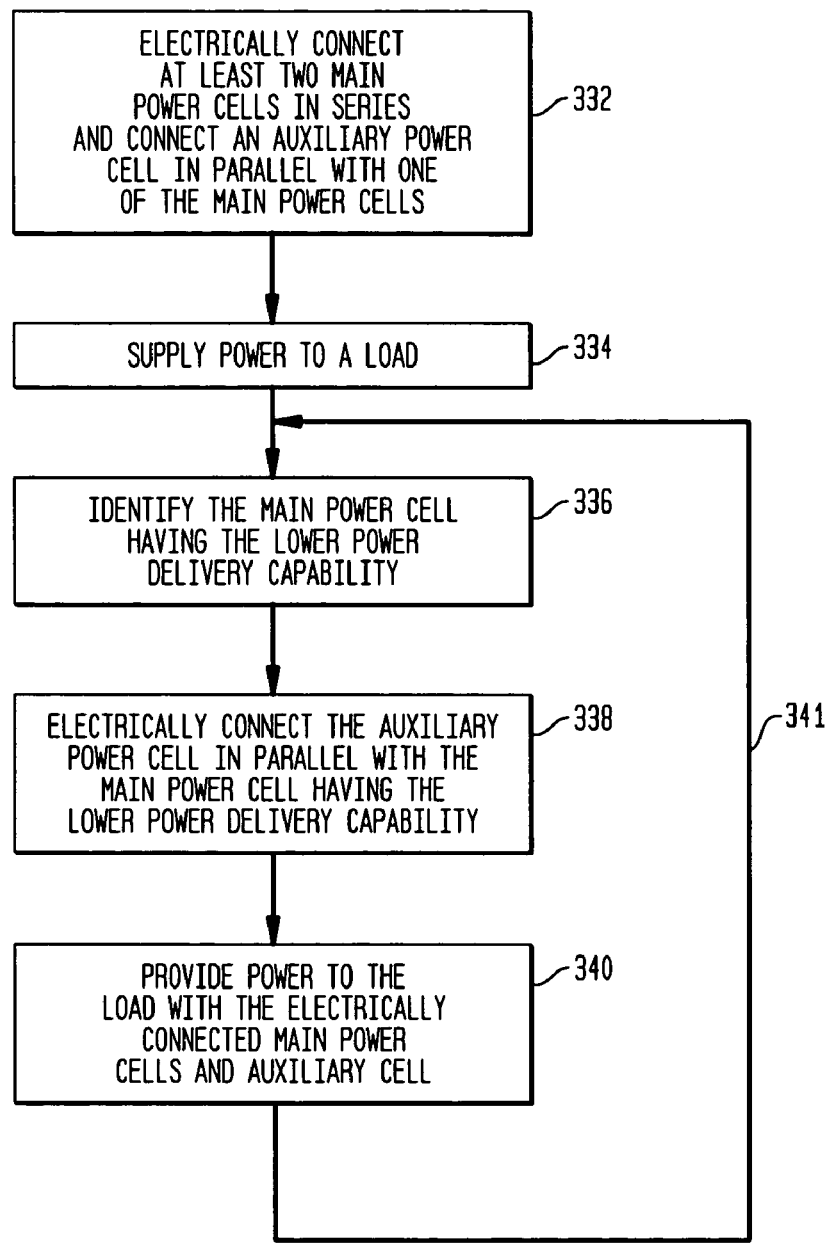

POWER SUPPLY HAVING AN AUXILIARY POWER CELL

CROSS-REFERENCE TO RELATED APPLICATIONS

This application is a continuation-in-part of U.S. patent application Ser. No. 11/645,729 filed on Dec. 27, 2006, now issued as U.S. Pat. No. 7,638,898, which is a Continuation of U.S. patent application Ser. No. 10/250,705 filed on Jul. 7, 2003, now issued as 7,157,808, which is a National Stage application of International Application PCT/AU2002/000074 filed on Jan. 24, 2002, which claims priority from Australian Patent Application PR 2693, which was filed on Jan. 24, 2001, all of which are hereby incorporated by reference herein.

BACKGROUND

1. Field of the Invention

The present invention relates generally to power supplies, and more particularly, to a power supply having an auxiliary power cell.

2. Related Art

Electrochemical power cells, solar power cells, fuel power cells, etc, (generally and collectively referred to as "power cells" herein) are used to generate and/or store electrical energy. One or more power cells are conventionally used to power a wide range of devices, equipment and structures. For example, it is well known to use a power supply having one or more power cells to power personal electronics such as portable audio players, cell phones, computers and the like, equipment such as cars or other machinery, and even structures, such as homes, offices, etc, (generally and collectively referred to as "powered systems" herein). Powered systems generally require the power supply to provide a threshold quantity of power to the system load (e.g. functional components) so that the powered system may operate effectively and consistently. For example, if a power supply provides insufficient power, a powered system may fail unexpectedly or erratically.

The ability of a power cell to output power, sometimes referred to as the power cells' power delivery capability, may be limited by the power cell's size, shape, type, condition, etc. As such, a plurality of power cells is typically electrically connected in series to supply sufficient power to the powered system. A particular problem associated with conventional power supplies is that failure of a single power cell may limit the power available to the powered system, thereby causing performance of the system to degrade, or causing unexpected system shutdown. For example, a decrease in the operating voltage of a single power cell could result in total system shutdown or failure. As used herein, the operating voltage of a power cell (sometimes simply "voltage" herein) refers to the voltage across the terminals of the power cell while the power cell is supplying power to a load.

In certain powered systems, loss or interruption of power results in, for example, total system failure, loss of information, or damage to the various components of the powered system. As such, unexpected or erratic failures, or failure to meet additional power demands, is undesirable, and, at times, unacceptable. Examples of powered systems in which such failures are often unacceptable include medical prostheses such as neural stimulators, pacers, drug pumps, hearing prostheses, and the like.

To avoid unexpected or erratic failure, certain powered systems alter or control the power consumption of the system when insufficient power is provided by the power cells. For example, certain powered systems successively implement a series of operational states each requiring less power than its immediate preceding state. Each state uses the remaining available power so that damage to the system or loss of information is reduced or eliminated prior to total system shut down. The power system may continue to operate in one of these states using the available power to operate only critical components, or the system may eventually shut down. Although damage to the powered system may be avoided, the ability to extend meaningful operation of the system beyond interruption of power is not possible.

SUMMARY

In accordance with aspects of the present invention, a power supply configured to supply power to a load is provided. The power supply comprises: a plurality of power cells electrically connected in series; an auxiliary power cell electrically connected in parallel with one of the plurality of power cells; a control module configured to selectively electrically connect the auxiliary cell in parallel with whichever one of the plurality of power cells has a lower power delivery capability.

In accordance with other aspects of the present invention, a method for supplying power to a load from a power supply comprising a plurality of power cells and an auxiliary power cell is provided. The method comprises: electrically connecting the plurality of power cells in series; determining which of the plurality of power cells has a lower power delivery capability; electrically connecting an auxiliary power cell in parallel with one of the plurality of power cells; and supplying the power to the load with the electrically connected power cells.

BRIEF DESCRIPTION OF THE DRAWINGS

Illustrative embodiments of the present invention are described herein with reference to the accompanying drawings, in which:

FIG. 3A is a high level flowchart illustrating one method for supplying power in accordance with embodiments of the present invention;

FIG. 3C is a detailed level flowchart illustrating another method for supplying power in accordance with embodiments of the present invention;

DETAILED DESCRIPTION

Figure 1:
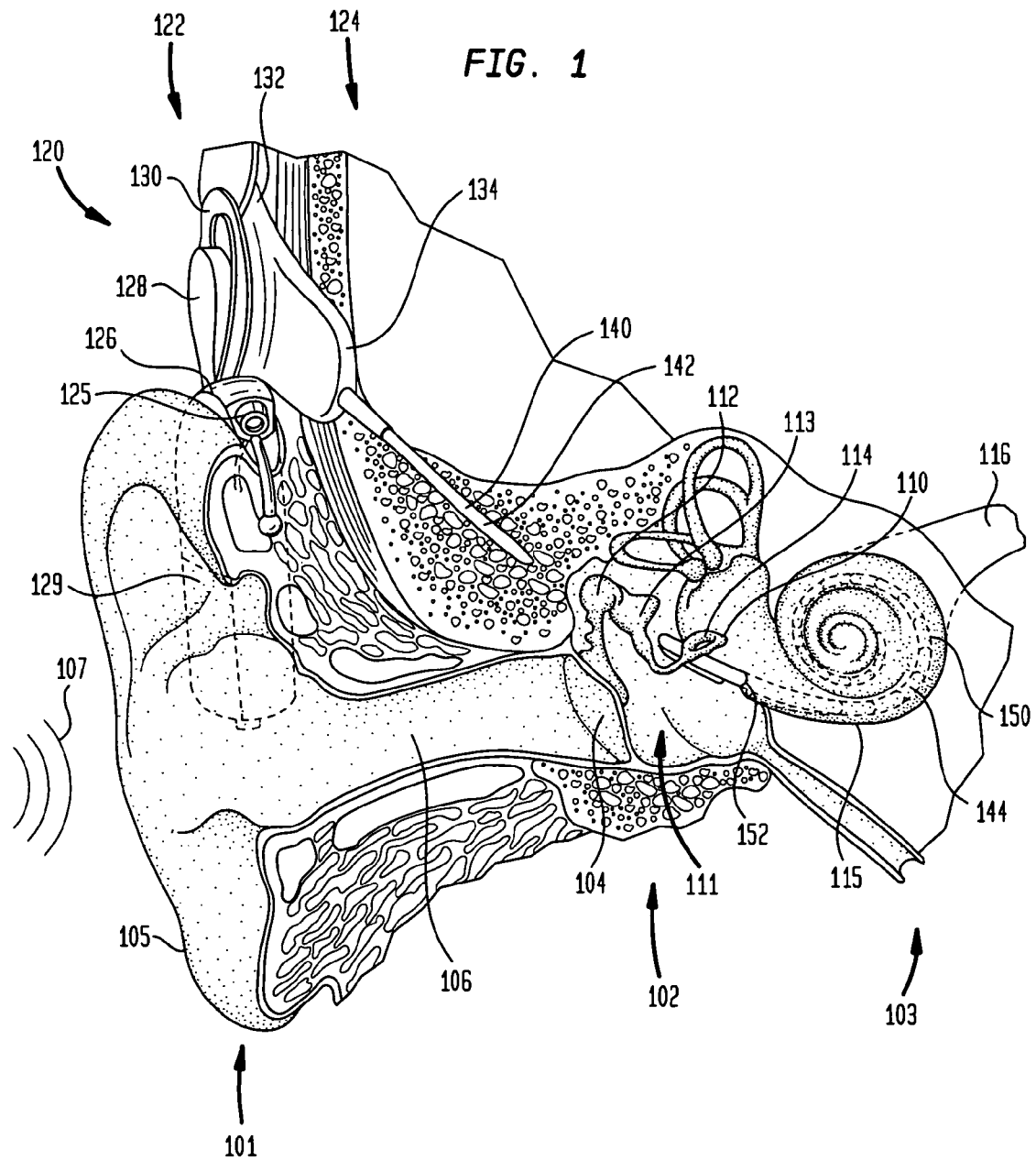
FIG. 1 is a perspective view of an exemplary powered system, specifically, a medical prosthesis known as a cochlear implant, in which embodiments of the present invention may be advantageously implemented.

Aspects of the present invention are generally directed to a power supply having selectively electrically connectable power cells to supply power to a load. The power supply comprises a plurality of power cells electrically connected in series with one another, (sometimes referred to herein as "serially connected power cells" or as a "series configuration of power cells"), and an auxiliary power cell connected in parallel with one of the serially connected power cells. A control module selectively connects the auxiliary cell in parallel with whichever one of the serially connected power cells has a lower power delivery capability. In accordance with embodiments of the present invention, the power delivery capability of the serially connected power cells may be re-evaluated to determine which power cell currently has the lower power delivery capability.

In one embodiment, the power delivery capability of a power cell is determined by measuring the operating voltage of a power cell. In other embodiments, the power delivery capability is determined by measuring the voltage of a power cell during a discharging and/or charging operation.

As noted above, power cells generate and/or store electrical energy and are used to power a wide range of powered systems. Although the present invention will be described herein with reference to supplying power to one particular type of powered system, namely an implantable medical device known as a cochlear implant, it should be appreciated that embodiments of the present invention may be used to supply power to any powered system.

Cochlear implants (also commonly referred to as cochlear prostheses, cochlear devices, cochlear implant devices, and the like; generally and collectively referred to herein as "cochlear implants") have been developed for hearing impaired individuals who are unable to derive suitable benefit from acoustic hearing aids. Cochlear implants include an array of stimulation electrodes which is implanted in the cochlea of the patient (referred to herein as a recipient). The electrode array is controlled by an electronic system encased in a hermetically sealed, biocompatible housing typically implanted in the mastoid. The electronic system, commonly referred to as a stimulator unit, essentially contains decoder and driver circuits for the stimulation electrodes. Acoustic sound reception and conversion of acoustic signals into electrical signals typically occurs in a speech processor. The speech processor may be worn by the recipient or may be implanted in the recipient. A microphone is located outside of the recipient's body, typically in a behind-the-ear housing worn on the auricle. Such a cochlear implant bypasses the hair power cells in the cochlea by directly delivering electrical stimulation to the auditory nerve fibers via the implanted electrode assembly. This enables the brain to perceive a hearing sensation resembling the natural hearing sensation normally delivered to the auditory nerve.

FIG. 1 is perspective view of one embodiment of a cochlear implant 100 implanted in a human cochlea with which embodiments of the present invention may be advantageously implemented. The relevant components of outer ear 101, middle ear 105 and inner ear 107 are described next below. Outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate. Such vibration sets up waves of fluid motion within cochlea 140. Such fluid motion, in turn, activates tiny hair power cells (not shown) that line the inside of cochlea 140. Activation of the hair power cells causes appropriate nerve impulses to be transferred through the spiral ganglion power cells and auditory nerve 114 to the brain, where they are perceived as sound.

Cochlear implant 100 comprises external component assembly 142 which is directly or indirectly attached to the body of the recipient, and an internal component assembly 144 which is temporarily or permanently implanted in the recipient. External component 142 may comprise a microphone 124 for detecting sound, an external housing 126 having speech processing elements therein, a power supply system (not shown), and an external transmitter unit 128. External transmitter unit 128 comprises an external coil 130 and, preferably, a magnet (not shown) secured directly or indirectly to external coil 130. The speech processing elements within housing 126 process the output of microphone 124 that is positioned, in the depicted embodiment, on auricle 110 of the recipient. The speech processing elements generate coded signals, referred to herein as a stimulation data signals, which are provided to external transmitter unit 128 via a cable (not shown).

Internal assembly 144 comprises an internal receiver unit 132, a stimulator unit 120, and an elongate electrode carrier 118. Internal receiver unit 132 comprises an internal transcutaneous transfer coil 136, and preferably, a magnet (also not shown) fixed relative to the internal coil. Internal receiver unit 132 and stimulator unit 120 are hermetically sealed within a biocompatible housing. Internal coil 136 receives power and stimulation data from external coil 130, as noted above. Elongate electrode carrier 118 has a proximal end connected to stimulator unit 120 and extends from stimulator unit 120 to cochlea 140. Electrode carrier 118 is implanted into cochlea 104 via a cochleostomy 122.

Electrode carrier 118 comprises an electrode array 146 disposed at the distal end thereof Electrode array 146 comprises a plurality of longitudinally-aligned electrodes 148. Stimulation signals generated by stimulator unit 120 are applied by electrodes 148 to cochlear 140, thereby stimulating auditory nerve 114.

In one embodiment, external coil 130 transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 101 of the recipient.

As noted, cochlear implant 100 may include a power supply that supplies power to the other components of cochlear implant 100. The power supply may be included in external component assembly 142 or in internal component assembly 144.

Figure 2:
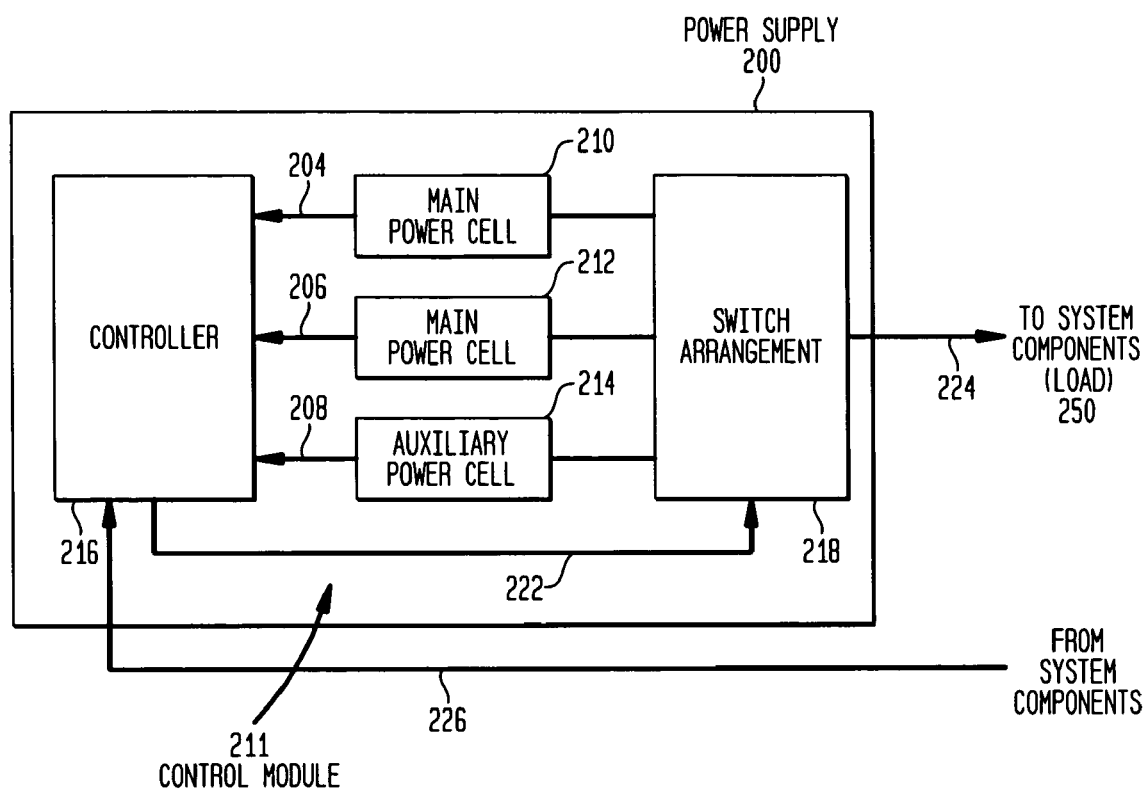
FIG. 2 is a functional block diagram of a power supply in accordance with embodiments of the present invention.

FIG. 2 is a functional block diagram of a power supply 200 in accordance with embodiments of the present invention. Power supply 200 may be used to provide power to a load, such as one or more power dissipating components of cochlear implant 100, referred to herein as load 250. In the exemplary illustrated embodiment, power supply 200 comprises a control module 211, main power cells 210, 212, and an auxiliary power cell 214. Control module 211 comprises a controller 216 and a switch arrangement 218.

Auxiliary power cell 214 is electrically connected in parallel with one or more of main power cells 210, 212 such that cells 210, 212 and 214 collectively supply power to load 250. As described below in more detail, auxiliary cell 214 is electrically connected in parallel with whichever of main cells 210, 212 has a lower power delivery capability. In one embodiment, the power delivery capability of a main power cell 210, 212 is determined by measuring the operating voltage of the power cell. As described in more detail, this determination may be made, for example, by comparing the operating voltages of main cells 210, 212 to one another. In other embodiments, the power delivery capability of a main power cell 210, 212 is determined by measuring the voltage of a power cell during a discharging and/or charging operation.

In such embodiments, comparison of the power delivery capabilities of main cells 210, 212 may be made by control module 211. For example, in one embodiment, one or more components of control module 211, such as controller 216, compare the power delivery capabilities of main power cells 210, 212 to one another. Based on this comparison, controller 216 sends a control signal 222 to switch arrangement 218 so as to connect auxiliary power cell 214 in parallel with whichever of main power cells 210, 212 has the lower power delivery capability.

In embodiments of the present invention, the power delivery capabilities of main cells 210, 212 may be re-evaluated. Control module 211 may then continually monitor or periodically evaluate the performance of main cells 210, 212 to determine which main cell has a lower power delivery capability. As such, auxiliary cell 214 may be controllably and alternatively connected in parallel with whichever of main power cells 210, 212 has the lower power delivery capability.

In embodiments of the present invention, the determination of which of main cells 210, 212 has a lower power delivery capability is performed during, or immediately following initialization of power supply 200 so that auxiliary cell 214 is continually electrically connected in parallel with one of the main power cells.

In some embodiments the determination of which of main cells 210, 212 has a lower power delivery capability may occur following a determination that the power demands of load 250 exceed the power 224 collectively output by main cells 210, 212. For example, in such embodiments, if control module 211 determines that the power demands of load 250 exceed power 224, control module 211 evaluates the performance of main cells 210, 212. Based on this evaluation, control 211 electrically connects auxiliary power cell 214 in parallel with one of main power cells 210, 212. In such embodiments, the determination that the power demands of load 250 exceed power 224 may be based on the current or future power demands of the load, the power currently or subsequently output by the series configuration, and/or combinations thereof.

Control module 211 determines that the power demands of load 250 exceed power 224 based on information 204 and 206 received from main power cells 210, 212, and/or information 226 received from load 250 or other system components. Power supply 200 may include any combination of hardware or software which measures or otherwise obtains the desired information from main power cells 210, 212, load 250, or other system components. Control module 211 may further implement one or more algorithms which estimate or otherwise determine the current or future power demands of load 250, or the current or future power output by the series configuration of main power cells 210, 212, based on, for example, the received information.

In the embodiment illustrated in FIG. 2, control module 211 has been illustrated integrated with power supply 200. It should be appreciated that in other embodiments one or more components of control module 211 may be physically separate from power supply 200.

In the described embodiment, switch arrangement 218 may comprise one or more circuit elements which electrically connect auxiliary cell 214 in parallel with one or more main cells 210, 212. However, it should be appreciated that in other applications switch arrangement 218 is not limited to circuit elements. For example, switch arrangement may comprise any types of switches, relays or other element which electrical connect auxiliary cell 214 in parallel with one or more main cells 210, 212.

FIG. 3A is a high level flowchart illustrating one method for supplying power in accordance with embodiments of the present invention. In the illustrated embodiment, at block 304, at least two main power cells are electrically connected in series with each other, and an auxiliary cell connected in parallel with one of the main power cells collectively supply power to a load. At block 308, the method ensures that the auxiliary power cell is connected in parallel with one of the serially connected main power cells having a lower power delivery capability. Thereafter, at block 310, electrically connected main power cells and the auxiliary power cell collectively supply power to the load. As shown in FIG. 3C, the power delivery capabilities of the serially connected main cells may be re-evaluated. As such, the auxiliary cell may be controllably and alternatively connected in parallel with whichever of the main power has the lower power delivery capability. This re-evaluation process may continue indefinitely during operation of the power supply.

Figure 3B:
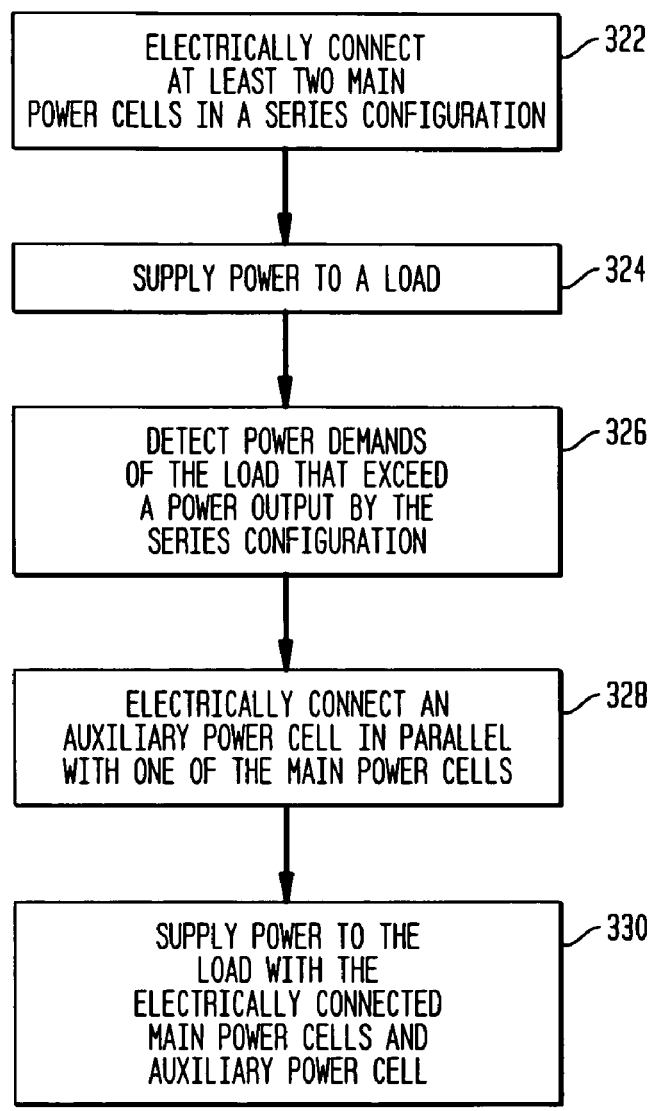
FIG. 3B is a detailed level flowchart illustrating one method for supplying power in accordance with embodiments of the present invention.

FIG. 3B is a detailed level flowchart illustrating one method for supplying power in accordance with certain embodiments of the present invention. At block 322 at least two main power cells are electrically connected in series. At block 324, the series configuration of main power cells supplies power to a load. At block 326, power demands of the load are detected which exceed the power supplied by the serially connected power cells. Following this detection, at block 328 an auxiliary power cell is connected in parallel with one of the serially connected main power cells. As described above, the auxiliary power cell may be connected in parallel with, for example, the main power cell having a lower power delivery capability.

Thereafter, at block 313, the electrically connected auxiliary power cell and main power cells collectively supply power to the load. Also as described above, the power delivery capabilities of the serially connected main cells may be re-evaluated. As such, the auxiliary cell may be controllably and alternatively connected in parallel with whichever of the main power has the lower power delivery capability.

FIG. 3C is a detailed level flowchart illustrating another method for supplying power in accordance with embodiments of FIG. 3A. At block 332 at least two main power cells are electrically connected in series, and an auxiliary power cell is connected in parallel with one of the main power cells. At block 334, the electrically connected power cells supply power to a load. At block 336, a main power cell having the lower power delivery capability is identified. Details of identifying the main power cell having a lower power delivery capability are provided below with reference to FIGS. 4A-4C. At block 338 the auxiliary power cell is connected in parallel with the main power cell identified as having the lower power delivery capability. Thereafter, at block 340, the electrically connected main power cells and auxiliary power cell collectively supply power to the load. It should be appreciated that in some embodiments of the present invention, the operations described with reference to blocks 334-340 may be performed during initialization or start-up of the power supply or of a powered system to which the power supply is connected.

Following connection of the auxiliary cell in parallel with one of the main power cells, the power delivery capability of the serially connected main cells may be re-evaluated. As such, the auxiliary cell may be controllably and alternatively connected in parallel with whichever of the main power has the lower power delivery capability.

Figure 4A:
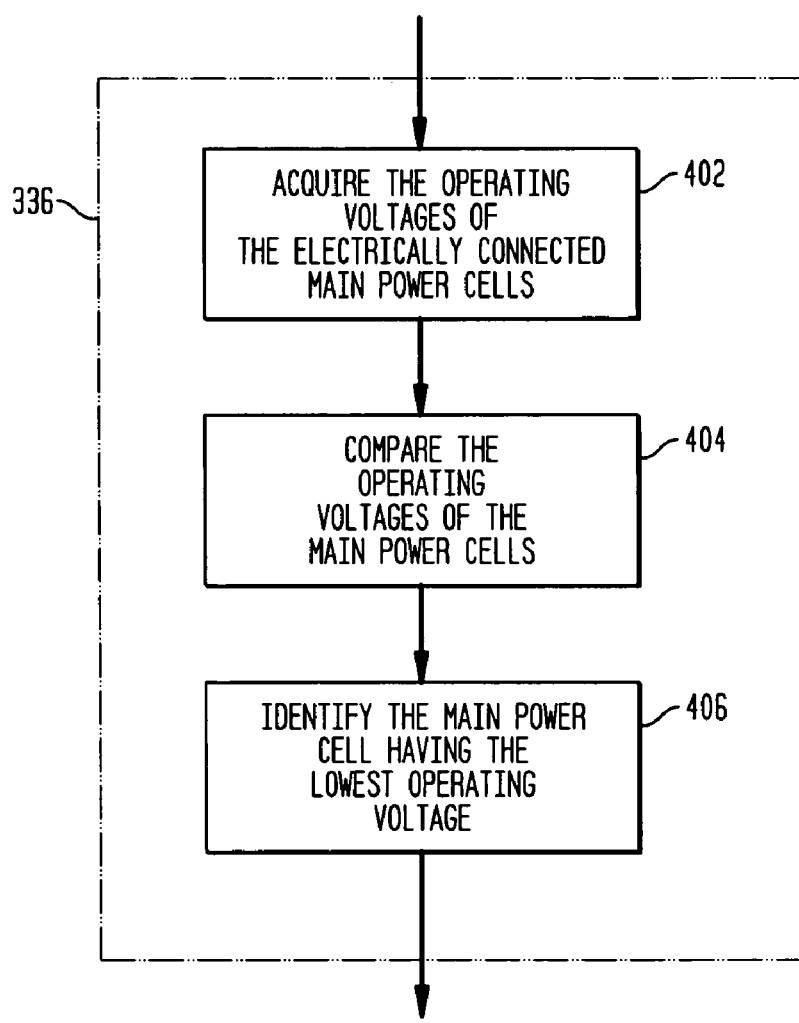
FIG. 4A is a detailed level flowchart illustrating the operations performed for identifying a main power cell in accordance with one embodiment of the present invention.

FIG. 4A is a detailed level flowchart illustrating the operations performed at block 336 of FIG. 3C for identifying the main power cell having the lower power delivery capability in accordance with an embodiment of the present invention. In the embodiment illustrated in FIG. 4A, the operating voltages of the main power cells are used to identify such a main power cell.

At block 402 the operating voltages of the electrically connected main power cells are received, acquired or otherwise obtained. At block 404, the operating voltages of the main power cells are compared to one another. The main power cell having the lower operating voltage is identified as the power cell having the lower power delivery capability.

Figure 4B:
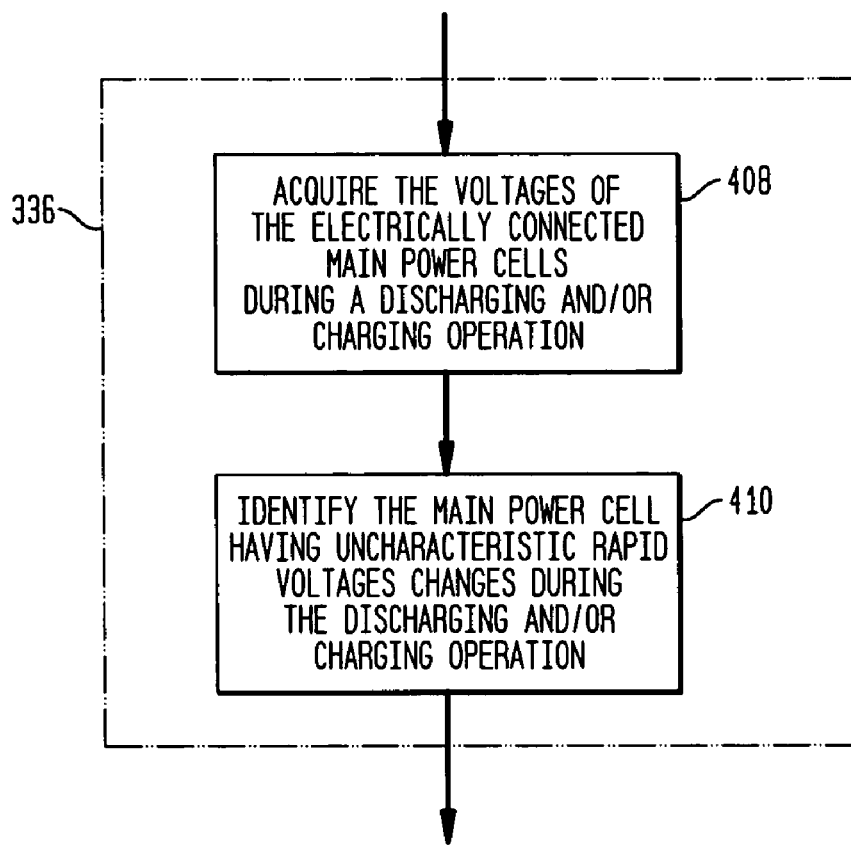
FIG. 4B is a detailed level flowchart illustrating the operations performed for identifying a main power cell in accordance with one embodiment of the present invention.

FIG. 4B is a detailed level flowchart illustrating the operations performed at block 336 of FIG. 3C in accordance with another embodiment of the present invention. At block 408 the voltage of each of the electrically connected main power cells are received, acquired or otherwise obtained during a discharging and/or discharging operation. At block 410, a main power cell having an uncharacteristically rapid voltage change during a discharging and/or charging operation is identified as the power cell having the lower power delivery capability.

Figure 4C:
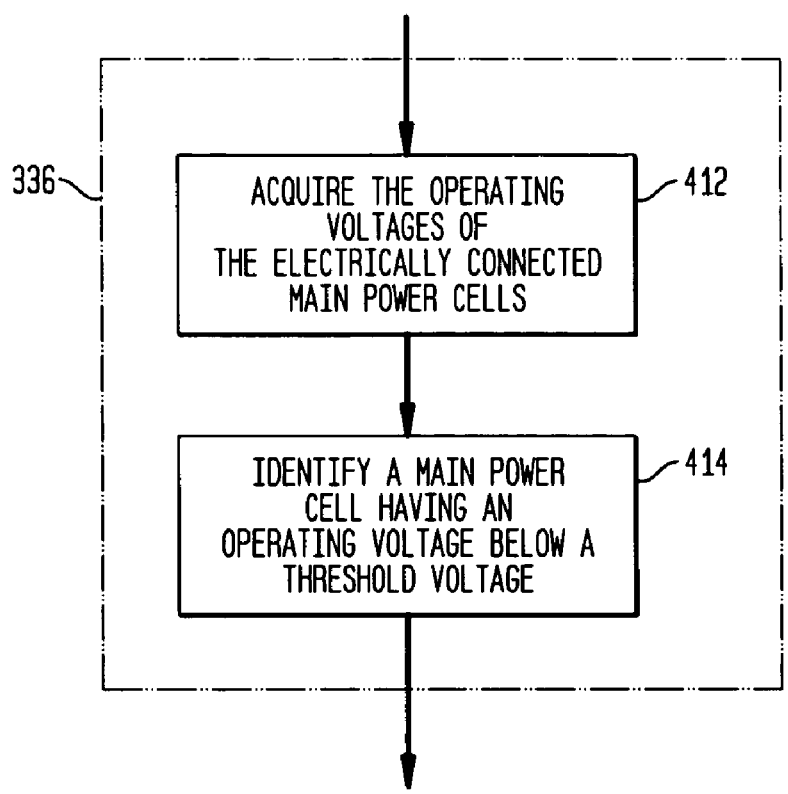
FIG. 4C is a detailed level flowchart illustrating the operations performed for identifying a main power cell in accordance with one embodiment of the present invention.

FIG. 4C is a detailed level flowchart illustrating the operations performed at block 336 of FIG. 3C in accordance with another embodiment of the present invention. At block 412 the operating voltages of the electrically connected main power cells are acquired. At block 414 a main power cell having the lower power delivery capability is identified by comparing the operating voltages to a threshold voltage.

As would be appreciated by one of ordinary skill in the art, any of the embodiments illustrated in FIGS. 4A-4C may be implemented by a power supply alone, on in combination with other embodiments.

Figure 5A:
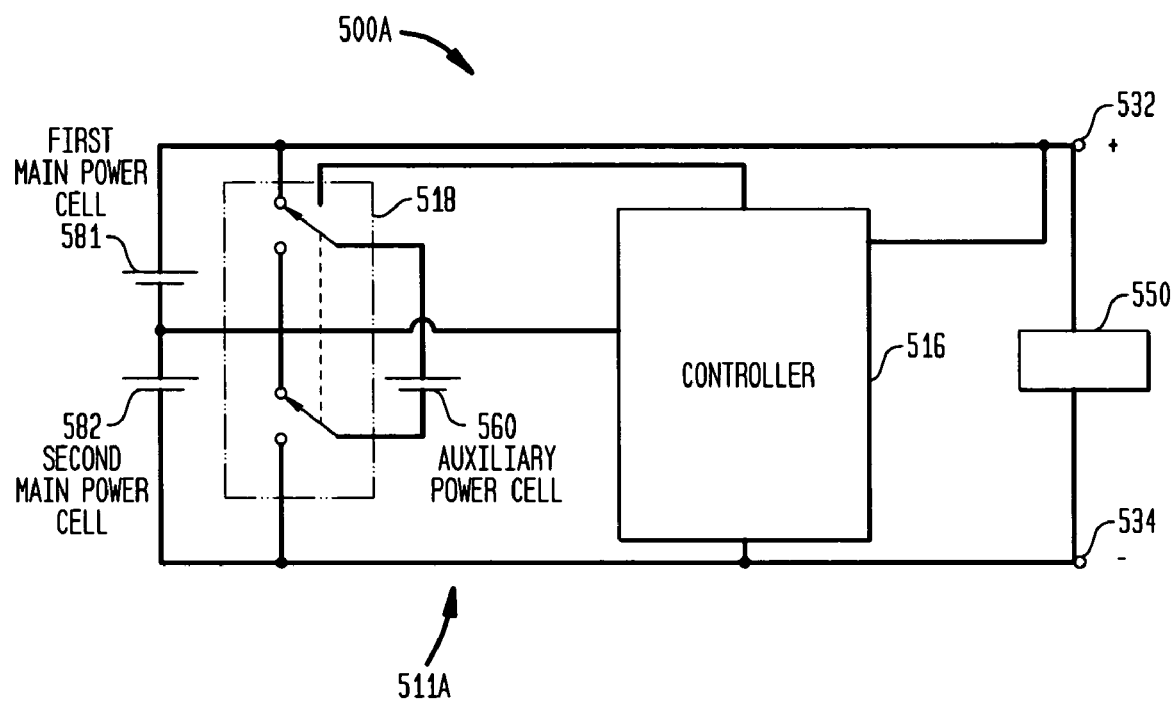
FIG. 5A is a schematic diagram illustrating a power supply in accordance with embodiments of the present invention.

FIG. 5A is a schematic diagram illustrating a power supply 500A in accordance with embodiments of the present invention. In the illustrated embodiments, power supply 500A comprises first main power cell 581, a second main power cell 582, an auxiliary power cell 560 and a control module 511A. Control module 511A comprises a controller 516 and a switch arrangement 518. Auxiliary power cell 560 is electrically connected in parallel with one of main power cells 581, 582 such that power cells 560, 581 and 582 collectively supply power to a load 550.

Auxiliary cell 560 is electrically connected in parallel with whichever of main cells 581, 582 has a lower power delivery capability. In one embodiment, the power delivery capability of a main power cell 581, 582 is determined by measuring the operating voltage of the power cell. As described above, this determination may be made, for example, by comparing the operating voltages of main cells 581, 582 to one another. In other embodiments, the power delivery capability of a main power cell 581, 582 is determined by measuring the voltage of a power cell during a discharging and/or charging operation.

Comparison of the power delivery capabilities of main cells 581, 582 may be made by control module 511A. For example, in one embodiment, one or more components of control module 511A, such as controller 516, compare the operating voltages of main power cells 581, 582 and sends a control signal to switch arrangement 518 so as to connect auxiliary power cell 560 in parallel with whichever of main power cells 581, 582 has the lower operating voltage.

In embodiments of the present invention, the power delivery capabilities of main cells 581, 582 may be re-evaluated. As such, auxiliary cell 560 may be controllably and alternatively connected in parallel with whichever of main power cells 581, 582 has the lower power delivery capability. This process of selectively connecting auxiliary power cell 560 in parallel with whichever one of the of main power cells 581, 582 having a lower voltage may continue indefinitely during operation of power supply 500A.

In embodiments of the present invention, the determination of which of main cells 581, 582 has a lower power delivery capability is performed during commencement of operation of power supply 500 so that auxiliary cell 560 is continually electrically connected in parallel with one of the main power cells. Control module 511A may continually monitor or periodically evaluate the performance of main cells 581, 582 to determine which main cell has a lower power delivery capability.

As described above with reference to FIG. 3B, in some embodiments, the determination of which of main cells 581, 582 has a lower power delivery capability may occur following an additional determination that the power demands of load 550 exceed the power output by main cells 581, 582. The determination that the power demands of load 550 exceed the power output by the series configuration may be based on the current or future power demands of the load, the power currently or subsequently output by the series configuration, and/or combinations thereof.

Control module 511A determines that the power demands of load 550 exceed the power output by the series configuration based on information received from main power cells 581, 582 and/or information received from load 550 or other system components. Power supply 500A may include any combination of hardware or software which measures or otherwise obtains the desired information from main power cells 581, 582, load 550, or the other system components. Control module 511A may further implement one or more algorithms which estimate or otherwise determine the current or future power demands of load 550, or the current or future power output by the series configuration of main power cells 581, 582, based on, for example, the received information.

In embodiments described above, switch arrangement 518 may comprise one or more circuit elements which electrically connect auxiliary cell 560 in parallel with one or more main cells 581, 582. For example, switch arrangement may include a double pole changeover switch to electrically connected the auxiliary cell in parallel with one or more of main cells 581, 582. As shown in FIG. 5A, the a double pole changeover switch may be ganged. It should be appreciated that in other applications switch arrangement 518 is not limited to circuit elements. For example, switch arrangement may comprise any types of switches, relays or other element which electrically connects auxiliary cell 560 in parallel with one or more main cells 581, 582.

Furthermore, as would be appreciated by one of ordinary skill in the art, control module 511A may comprise any combination of hardware and/or software configured to perform the operations described above. For example, in certain embodiments, control module 511A may include a comparator and other associated circuitry. In one such embodiment, the comparator may comprise a low-power comparator. This exemplary arrangement is described in commonly owned co-pending U.S. patent application Ser. No. 11/645,729 from which the present application claims priority, the contents of which are hereby incorporated by reference, In other embodiments, control module 511A may comprise a microprocessor having an Analog to Digital Converter (ADC) or multiplexer (MUX) and other associated circuitry. In these embodiments, the microprocessor and associated circuitry monitor the voltages of main power cells 581, 582 to selectively connect auxiliary power cell 560 in parallel with one of the main power cells.

In embodiments of the present invention, connection of auxiliary power cell 560 in parallel with one of main power cells 581, 582 may reduce the power supplied by the main power cell connected in parallel with the auxiliary cell. By reducing the power supplied by a main power cell, the operational life of the power cell may be extended. As such, as described in detail above, control module 516 is configured to alternate or otherwise vary the main power cell 581, 582 with which auxiliary power cell 560 is connected in parallel with.

For example, when auxiliary power cell 560 is connected in parallel with a first one of main power cells 581, 582, an increased power demand may be placed on the other main power cell. As such, after a period of time, auxiliary power cell 560 may be disconnected from the first main power cell 581 or 582 and connected in parallel with the other the main power cell. This process could continue so that the stored charge of main power cells 581 and 582 are depleted at approximately the same rates.

The determination to alternate or change the main power cell with which auxiliary power cell is connected in parallel may be made in any of the manners described above. Furthermore, hysteresis may be incorporated into the determination so as to limit the rate of switching of connection of auxiliary power cell 560 with main power cells 581, 582.

In certain embodiments, when auxiliary power cell 560 is connected in parallel with a main power cell 581, 582, the parallel connection permits recovery of the main power cell. For example, in one such embodiment, while auxiliary power cell 560 is connected with the identified main power cell, the identified main power cell is permitted to recover. In certain embodiments, the main power cell may be recharged.

In particular embodiments of the present invention, when auxiliary power cell 560 is connected in parallel with one of main power cells 581, 582, the main power cell may be electrically disconnected from the other of main power cells 581, 582 and auxiliary power cell 560. In these embodiments, following disconnection of the one main power cell, auxiliary power cell 560 is used to substantially replace the disconnected main power cell. Such an arrangement permits a disconnected main power cell to be replaced or otherwise removed from use without cessation of power to load 550.

Figure 5B:
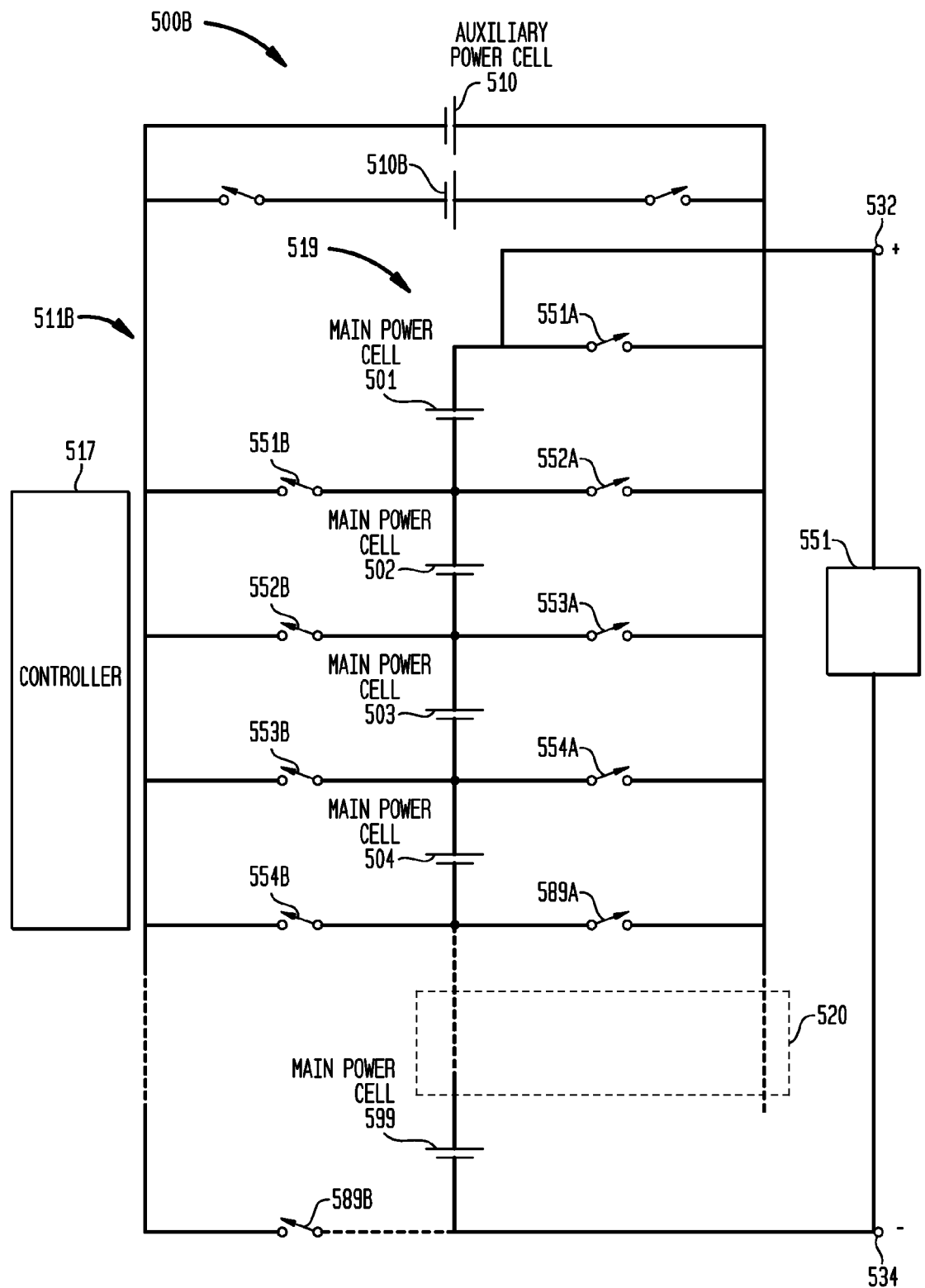
FIG. 5B is a schematic diagram illustrating a power supply in accordance with embodiments of the present invention.

FIG. 5B is a schematic diagram illustrating a power supply 500B in accordance with embodiments of the present invention. Power supply 500B comprises a plurality of main power cells 501-599, an auxiliary power cell 510, and a control module 511B. Control module 511B comprises a controller 517 and a switch arrangement 519.

As shown in FIG. 5B, five power cells, power cells 501, 502, 503, 504 and 599 are connected in series. However, it should be appreciated that fewer or additional power cells may be also be connected in series. For ease of illustration, optional additional power cells are shown as block 520.

Auxiliary power cell 510 is electrically connected in parallel with one of main power cells 501-599 such that power cells 510 and 501-599 collectively supply power to a load 551. Auxiliary cell 510 is electrically connected in parallel with whichever of main cells 501-599 has a lower power delivery capability. In one embodiment, the power delivery capability of a main power cell 501-599 is determined by measuring the operating voltage of the power cell. As described above, this determination may be made, for example, by comparing the operating voltages of main cells 501-599 to one another. In other embodiments, the power delivery capability of a main power cell 501-599 is determined by measuring the voltage of a power cell during a discharging and/or charging operation.

Comparison of the power delivery capabilities of main cells 501-599 may be made by control module 511B. For example, in one embodiment, one or more components of control module 511B, such as controller 517, compare the operating voltages of main power cells 501-599 and send a control signal to switch arrangement 519 so as to connect auxiliary power cell 510 in parallel with whichever of main power cells 501-599 has the lower operating voltage.

In embodiments of the present invention, the power delivery capabilities of main cells 501-599 may be re-evaluated. As such, auxiliary cell 510 may be controllably and alternatively connected in parallel with whichever of main power cells 501-599 has the lower power delivery capability.

In embodiments of the present invention, the determination of which of main cells 501-599 has a lower power delivery capability is performed during commencement of operation of power supply 500A so that auxiliary cell 510 is continually electrically connected in parallel with one of the main power cells. Control module 511B may continually monitor or periodically evaluate the performance of main cells 501-599 to determine which main cell has a lower power delivery capability.

As described above with reference to FIG. 3B, in some embodiments, the determination of which of main cells 501-599 has a lower power delivery capability may occur when the power demands of load 551 exceed the power output by main cells 501-599. The determination that the power demands of load 551 exceed the power output by the series configuration may be based on the current or future power demands of the load, the power currently or subsequently output by the series configuration, and/or combinations thereof.

Control module 511B determines that the power demands of load 551 exceed the power output by the series configuration based on information received from main power cells 501-599 and/or information received from load 551 or other system components. Power supply 500B may include any combination of hardware or software which measures or otherwise obtains the desired information from main power cells 501-599, load 551, or other system components. Control module 511B may further implement one or more algorithms which estimate or otherwise determine the current or future power demands of load 551, or the current or future power output by the series configuration of main power cells 501-599, based on, for example, the received information.

In the above described embodiments, switch arrangement 519 may comprise one or more circuit elements which electrically connect auxiliary cell 510 in parallel with one or more main cells 501-599. However, it should be appreciated that in other applications switch arrangement 519 is not limited to circuit elements. For example, switch arrangement may comprise any types of switches, relays or other element which electrically connects auxiliary cell 510 in parallel with one or more main cells 501-599.

As would be appreciated by one of ordinary skill in the art, control module 511B may take any combination of hardware and/or software configured to perform the operations/functions described above. For example, control module 511B may comprise a microprocessor having an Analog to Digital Converter (ADC) or multiplexer (MUX) and other associated circuitry.

For ease of illustration, FIG. 5B illustrates the use of only two auxiliary power cells 510. However, it should be appreciated that only one, or additional auxiliary power cells may also be incorporated in power supply 500B. In such embodiments, each auxiliary power supply may be configured to be connected in parallel with one or more of main power cells 501-599. Also, in certain embodiments, multiple auxiliary power cells may be connected in parallel with one another and/or a main power cell 501-599. Also, in certain embodiments, multiple auxiliary power cells may be connected in parallel with one another and/or a main power cell 501-599. For example, in certain embodiments, an additional auxiliary power cell and power cell 510 may both be connected in parallel with a main power cell 501-599 having a lower power delivery capability then other main power cells. In other embodiments, an additional power cell may be connected with a main power cell 501-599 which does not have a lower power delivery capability when compared to other main power cells. Various other combinations and usage of additional auxiliary power cells are within the scope of this invention.

For ease of illustration, controller 517 of control module 511B has been shown disconnected from switch arrangement 519. However, it should be appreciated that controller 517 may be connected to switch arrangement 519 via one or more control lines to provide control of switches 551-589.

Connection of auxiliary power cell 510 in parallel with one of main power cells 501-599 may reduce the power supplied by the main power cell connected in parallel. By reducing the power supplied by a main power cell, the operational life of the power cell may be extended. As such, in certain embodiments of the present invention, control module 511B is configured to alternate or otherwise vary the main power cell 501-599 with which auxiliary power cell 510 is connected in parallel with.

For example, in one embodiment, when auxiliary power cell 510 is connected in parallel with a first one of main power cells 501-599, an increased power demand may be placed on one or more of the other main power cells. As such, after a desired time period, the auxiliary power cell may be disconnected from the first one of main power cells 501-599 and connected in parallel with another main power cell. This process could continue so that the stored charges of main power cells 501-599 are depleted at approximately the same rates.

The determination to alternate or change the main power cell with which auxiliary power cell is connected in parallel may be made in any of the manners described above. Furthermore, hysteresis may be incorporated into the determination so as to limit the rate of switching of auxiliary power cell 510 between the various configurations.

In certain embodiments, when auxiliary power cell 510 is connected in parallel with a main power cell 501-599, the parallel connection permits recovery of the main power cell. For example, in certain embodiments of the present invention, during the parallel connection, the identified main power cell is permitted to recover. In certain embodiments, the power cell may be recharged.

In particular embodiments of the present invention, when auxiliary power cell 510 is connected in parallel with one of main power cells 501-599, control module 511B determines that the main power cell which is connected in parallel with auxiliary power cell 510 should be electrically disconnected from the other of main power cells 501-599 and auxiliary power cell 510. In these embodiments, following disconnection of the one main power cell, auxiliary power cell 510 is used to substantially replace the disconnected main power cell.

Embodiments of the present have been described above with reference to power cells. Such power cells may include, for example, solar power cells, electrochemical power cells such as Zinc Air, lead acid, NiMH, NiCd, Lion, Plion, Alkaline, or Carbon Zinc power cells, semiconductor power cells, and the like. Power cells in accordance with the present invention may also include both primary and rechargeable power cells.

Furthermore, as would be appreciated by one of ordinary skill in the art, a battery simply refers to two or more power cells connected in series. As such, embodiments of the present invention may be equally implemented by substituting a battery for a power cell or plurality of power cells. In such embodiments, an auxiliary power cell, or auxiliary battery would be connected in parallel with one or batteries in the manners described above.

In certain embodiments of the present invention, the power cells are preferably all of the same design. However, in other embodiments of the present invention, different types of power cells may used together. For example, in one such embodiment, the main power cells could NiMH power cells and a Zinc Air power cell could be used as the auxiliary power cell. In certain such embodiments, the Zinc Air power cell may charge the NiMH main power cells.

As noted above, an auxiliary power cell is connected in parallel with a main power cell having a lower power delivery capability. As described herein, the information relied upon to make this determination may include, for example, the operating voltages of the main power cells and/or the voltages of the power cells during a charging or discharging operation. In certain applications, additional information may be used. For example, in one embodiment, the temperature of a power cell may be monitored. In such embodiments, if the temperature of the power cell rises above a predetermined temperature, or if a rapid temperature change would be experienced by the power cell, a determination could be made that the cell has a a lower power delivery capability than other power cells.

As noted above, embodiments of the present invention may be used in a variety of applications and powered systems. For example, principles of the present invention may have application in the fields of electric cars, solar/wind power systems, or medical devices. As such, the type of switches used to connect an auxiliary power cell in parallel with a main power cell may vary greatly depending on, for example, the desired application, the type of powered system, the type of power cells, etc. Therefore, the utilized switches may comprise analog switches, mechanical contactors, MOSFETs, etc.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A cochlear implant comprising:
a power supply configured to supply power to one or more components of the cochlear implant, comprising:
a plurality of batteries electrically connected in series and configured to output power;
an auxiliary battery; and
a control module configured to measure power demands of said components, to evaluate respective power delivery capabilities of each of said plurality of batteries in response to a determination that the power output by said plurality of batteries is insufficient to meet the measured power demands of said components, and to selectively electrically connect said auxiliary battery in parallel with whichever one of said plurality of batteries has a lower power delivery capability than another of said plurality of batteries.

2. The cochlear implant of claim 1, wherein said control module electrically connects said auxiliary battery in parallel with whichever one of said plurality of batteries has a lower operating voltage than another of said plurality of batteries.

3. The cochlear implant of claim 2, wherein said control module is configured to determine which one of said plurality of batteries has said lower operating voltage by comparing the voltages of said plurality of batteries to one another.

4. The cochlear implant of claim 2, wherein said control module is configured to determine which one of said plurality of batteries has said lower operating voltage by comparing the voltages of said plurality of batteries to a threshold voltage.

5. The cochlear implant of claim 1, wherein each of said plurality of batteries experience voltage changes during normal charging and discharging operations, and wherein said control module is configured to determine which one of said plurality of batteries has said lower power delivery capability by identifying when one of said plurality of batteries experiences a change in voltage during one or more of a charging and discharging operation that is more rapid than voltage changes experienced during a normal charging or discharging operation.

6. The cochlear implant of claim 1, wherein said control module is configured to continually monitor the power delivery capabilities of said plurality of batteries.

7. The cochlear implant of claim 1, wherein said control module is configured to periodically evaluate the power delivery capabilities of said plurality of batteries.

8. The cochlear implant of claim 1, wherein said control module comprises:
a controller configured to evaluate the power delivery capabilities of said plurality of batteries; and
a switch arrangement configured to connect said auxiliary power cells battery in parallel with one of said plurality of batteries based on said evaluation by said controller.

9. The cochlear implant of claim 8, wherein said controller comprises a microprocessor.

10. The cochlear implant of claim 1, wherein said controller comprises a comparator.

11. The cochlear implant of claim 1, further comprising:
one or more additional auxiliary batteries, wherein said control module is configured to connect at least one of said one or more additional auxiliary batteries in parallel with a selected one of said plurality of batteries.

12. The cochlear implant of claim 11, wherein said selected one of said plurality of batteries is said battery having said lower power delivery capability.

13. The cochlear implant of claim 11, wherein said selected one of said plurality of batteries is one of said plurality of batteries that does not have said lower power delivery capability.

14. The cochlear implant of claim 1, wherein said cochlear implant is fully implantable.

15. The cochlear implant of claim 1, wherein said control module is configured to determine whether the measured power demands of the one or more components exceed the power output by said plurality of batteries.

16. A method for supplying power from a power supply in a cochlear implant to one or more components of the cochlear implant, wherein the power supply comprises a plurality of batteries electrically connected in series and configured to output power, and an auxiliary battery, the method comprising:
measuring, with said power supply, power demands of said one or more components;
determining, with said power supply, which of said plurality of batteries has the lowest power delivery capability, in response to a determination that the power output by said plurality of batteries is insufficient to meet the measured power demands of said components;
electrically connecting said auxiliary battery in parallel with said battery having said lowest power delivery capability; and
supplying said power to said one or more ether components with said electrically connected batteries.

17. The method of claim 16, wherein said determining which of said plurality of batteries has the lowest power delivery capability comprises:
measuring the operating voltages of said plurality of batteries; and
comparing said measured operating voltages to one another.

18. The method of claim 16, wherein each of said plurality of batteries experiences voltage changes during normal charging and discharging operations, and wherein said determining which of said plurality of batteries has the lowest power delivery capability comprises:
measuring the voltages of said plurality of batteries during one or more of a charging and discharging operation; and
determining that the voltage of one of said plurality of batteries experienced a voltage change that was more rapid than voltage changes experienced during a normal charging or discharging operation.

19. The method of claim 16, wherein said determining which of said plurality of batteries has the lowest power delivery capability comprises:
measuring the operating voltages of said plurality of batteries;
comparing said measured operating voltages to a threshold voltage; and
determining which of said plurality of batteries has an operating voltage which is below said threshold voltage.

20. The method of claim 16, further comprising:
continually re-evaluating the power delivery capabilities of said plurality of batteries.

21. The method of claim 16, further comprising:
periodically re-evaluating the power delivery capabilities of said plurality of batteries.

22. The method of claim 16, wherein said power supply further comprises one or more additional auxiliary batteries, the method further comprising:
- electrically connecting at least one of said one or more additional auxiliary batteries in parallel with a selected one of said plurality of batteries.

23. The method of claim 22, wherein said selected one of said plurality of batteries is said battery having said lowest power delivery capability.

24. The method of claim 22, wherein said selected one of said plurality of batteries is one of said plurality of batteries that does not have said lowest power delivery capability.

25. The method of claim 16, further comprising:
- determining, with said power supply, whether the measured power demands of the one or more components exceed the power output by said plurality of batteries.

* * * * *